(12) United States Patent
Manaresi et al.

(10) Patent No.: US 7,699,969 B2
(45) Date of Patent: Apr. 20, 2010

(54) METHOD AND APPARATUS FOR HIGH-THROUGHPUT BIOLOGICAL-ACTIVITY SCREENING OF CELLS AND/OR COMPOUNDS

(75) Inventors: Nicolò Manaresi, Bologna (IT); Gianni Medoro, Trinitapoli (IT); Luigi Altomare, Bologna (IT); Marco Tartagni, Meldola (IT); Roberto Guerrieri, Bologna (IT)

(73) Assignee: Silicon Biosystems S.p.A., Bologna (IT)

( * ) Notice: Subject to any disclaimer, the term of this patent is extended or adjusted under 35 U.S.C. 154(b) by 1752 days.

(21) Appl. No.: 10/476,467

(22) PCT Filed: May 2, 2002

(86) PCT No.: PCT/IT02/00285

§ 371 (c)(1),
(2), (4) Date: May 3, 2004

(87) PCT Pub. No.: WO02/088702

PCT Pub. Date: Nov. 7, 2002

(65) Prior Publication Data

US 2004/0191789 A1    Sep. 30, 2004

(30) Foreign Application Priority Data

May 2, 2001    (IT) .............................. TO01A0411

(51) Int. Cl.
*G01N 27/447* (2006.01)
*G01N 27/453* (2006.01)
(52) U.S. Cl. ...................... 204/547; 204/643
(58) Field of Classification Search ................ 204/164, 204/547, 554, 643, 660
See application file for complete search history.

(56) References Cited

U.S. PATENT DOCUMENTS 6,071,394 A * 6/2000 Cheng et al. ................. 204/547

(Continued)

FOREIGN PATENT DOCUMENTS

EP    0 815 942 A1    1/1998

(Continued)

OTHER PUBLICATIONS

Muller, T.; A 3-D microelectrode system for handling and caging single cells and particles; 1999; Elsevier; Biosesnsors and Bioelectronics; vol. 14; pp. 247-256.*

*Primary Examiner*—Alex Noguerola
(74) *Attorney, Agent, or Firm*—SEED IP Law Group PLLC

(57) ABSTRACT

First entities consisting in cells or microorganisms (BIO) and second entities consisting in compounds or compound units, carried typically by microbeads (BEAD), are trapped selectively within closed movable potential cages (S1) by means of dielectrophoretic force generated by mutually opposed electrodes (M1, M2). The cages are set in relative motion so as to bring about the interaction of selected first and second entities, causing the cages containing them to fuse, whereupon results are obtained preferably by reinstating the original cages and/or observing previously empty adjacent cages. The procedure takes place in a device (DE) with two separate chambers (F, FL) connected one to the other by way of a narrow passage (D) and finished with respective selectively controllable inlets and outlets (I1, I2; O1, O2) through which a liquid or semi-liquid buffer (L) can be pumped in or out.

43 Claims, 5 Drawing Sheets

U.S. PATENT DOCUMENTS

| | | | |
|---|---|---|---|
| 6,294,063 B1 * | 9/2001 | Becker et al. | 204/450 |
| 6,387,707 B1 * | 5/2002 | Seul et al. | 436/164 |
| 6,492,175 B1 * | 12/2002 | Muller et al. | 435/450 |
| 6,596,143 B1 * | 7/2003 | Wang et al. | 204/547 |
| 6,991,941 B1 * | 1/2006 | Seul | 436/534 |
| 7,081,192 B1 * | 7/2006 | Wang et al. | 204/547 |
| 2001/0047941 A1 * | 12/2001 | Washizu et al. | 204/547 |
| 2002/0076825 A1 * | 6/2002 | Cheng et al. | 436/174 |

FOREIGN PATENT DOCUMENTS

| | | |
|---|---|---|
| EP | 1 088 592 A2 | 4/2001 |
| WO | WO 99/38612 | 8/1999 |
| WO | WO 00/32744 | 6/2000 |
| WO | WO 00/47322 | 8/2000 |
| WO | WO 00/69565 | 11/2000 |

* cited by examiner

METHOD AND APPARATUS FOR HIGH-THROUGHPUT BIOLOGICAL-ACTIVITY SCREENING OF CELLS AND/OR COMPOUNDS

This application is a 371 of the International Application Number PCT/IT2002/000285, filed May 02, 2002, published as WO2002/088702 on Nov. 07, 2002, and the correction for the application published in Section II of the PCT Gazette on Jun. 24 2004 (to include the drawings), which claim foreign priority from Italian patent application TO01A000411, filed on May 02, 2001.

FIELD OF THE INVENTION

The present invention relates to a method of manipulating particles utilizing dielectrophoretic forces for screening procedures of high biological value conducted on prospective pharmaceutical compounds, applicable to diagnostic and agrifood analysis. The invention relates also to a device for implementation of the method disclosed.

BACKGROUND OF THE INVENTION

In an expanding art field that embraces the discovery of new drugs and combinatorial chemistry used in the preparation of new candidate compounds, it would be especially advantageous to be able to screen a great number of substances by way of a procedure affording high throughput, to the end of observing their physiological impact on animals and on humans. Before testing the efficacy of a drug candidate "partially successful" on animals, the substance should be tested for its potential toxicity in respect of living cells. Conversely, it is the conventional practice that promising compounds are tested almost immediately in extensive studies on animal models, studies which are at the same time lengthy and costly. Moreover, the practice of extensive testing on animals is becoming less and less acceptable culturally in the United States and in Europe. If prospective pharmaceutical compounds are tested to observe their interactions with living cells before studies are conducted on animal models, this can reduce the number of animals needed for subsequent trials by eliminating many of the candidates before the stage of testing on animals is reached.

Current procedures for the analysis of cell-drug interaction afford neither high throughput nor high biological value, due to the limited number of cells and compounds that can be analyzed in a given period of time, the scant practicality of the methods necessary for administering the compounds, and the considerable volumes of the compound required.

Accordingly, efforts have been made to overcome these drawbacks by studying alternative methods for the analysis of interactions between cell and drug, or more generally between biological samples and biologically active agents, such as those indicated below by way of example.

Cell Matrices

Several methods have been described for producing uniformly micro-modelled cell matrices, for example photolithography (Mrksich & Whitesides, Ann. Rev. Biophys. Biomol. Struc. 25:55-78, 1996). According to this method, which uses a glass plate, a photosensitive material and a mask are employed to obtain a plate presenting a matrix of reactive or hydrophilic spots on a surface which by contrast is hydrophobic. The matrix of hydrophilic groups provides a substrate on which to obtain a non-specific and non-covalent bond of certain types of cells, including those of neuronal origin (Kleinfeld et al., J. Neurosci. 8:4098-4120, 1988).

In another method based on specific but non-covalent interactions, photoprinting is used to produce a gold surface presenting spots of laminin, a cell-binding protein normally found in the extracellular matrix (Singhvi et al., Science 264: 696-698, 1994)

A more specific uniform bond can be obtained by crosslinking specific molecules, such as proteins, at reactive sites of the modelled substrate (Aplin & Hughes, Analyt. Biochem. 113: 144-148, 1981).

Another development of an optical system for modelling a substrate and creating reactive spots is based on the use of deep UV rays directed through an optical mask, to obtain active sites consisting in polar silanol groups. These groups make up the spots of the matrix and are modified further by being paired with other reactive groups, as disclosed in U.S. Pat. No. 5,324,591. This optical method of forming uniform cell matrices on a substrate requires fewer steps than the photolithography method, but requires ultraviolet light of high intensity, and suitable light sources are very costly.

In all these methods moreover, the resulting cell matrix is uniform, since the biochemically specific molecules are bound to the chemically micro-modelled matrices. With the photolithography method, the cells bind to matrices of hydrophilic spots and/or to specific molecules attached to the spots which bind the cells. Accordingly, the cells bind to all the spots of the matrix in the same way. With the optical method, the cells bind to matrices containing spots of free amino acid groups by adhesion. There is little or no difference between these spots. Here again, the cells bind to all the spots in the same way and it is possible only to study one given type of cell interaction using these matrices, since any one spot is essentially the same as another.

This type of matrix therefore lacks flexibility as an instrument for the analysis of a single specific variety of cell or interaction. Consequently, the need arises to produce cell matrices that are not uniformly micro-modelled, so as to increase the number of cells or interactions that can be analyzed simultaneously.

International patent applications WO 00/39587 and WO 00/47996 illustrate a system of sensors and methods for preparing matrices, composite or otherwise, of beads or cells ordered randomly on the tips of bundles of optical fibres. Whilst on the one hand the methods described in these applications offer great analytical potential, especially in the case of proteins and nucleic acids, there is the drawback that they allow the experimenter neither to separate nor, much less, to recover populations of interest that may be identified.

Cell Physiology and Fluorescence

Conducting a high throughput assay on many thousands of compounds requires the manipulation in parallel and the treatment of many compounds and of the reagents included in the assay; in addition, there must be a method of identifying and measuring the results of the experiment in the simplest way possible. The more common assays use homogeneous blends of compounds and biological reagents together with at least one marker compound, loaded into a standard 96 or 384-well microtiter plate (Kahl et al., J. Biomol. Scr. 2:3340, 1997). The signals measured from each well, whether emissions of fluorescence, optical density or radioactivity, are integrated with the signal from all the material occupying the well to give a general average of the population of all molecules in the well. This type of assay is commonly termed a homogeneous assay.

As fluorescence is among the systems most widely used, various methods have been developed for generating images of fluorescent cells with a microscope and extracting information on the spatial distribution and the changes occurring over time in these cells. Many of these methods and their applications are described in an article by Taylor et al., Am. Scientist 80: 322-335, 1992.

The proposed methods have been designed and optimized with the preparation of a small number of samples in view so that the distribution, quantity and biochemical profile of fluorescent reporter molecules present in the cells can be measured obtaining a high level of spatial and temporal resolution.

Useful methods of detection include treating the cells with colorants and fluorescent reagents to obtain images and/or genetically modify the cells in such a way that they will produce fluorescent proteins, like modified Green Fluorescent Protein (GFP). The use of GFP in the study of gene expression and the localization of proteins is discussed at length by Chalfic et al., in Science 263: 803-805.

Nonetheless, these methods are complex, costly and slow, and they can be used only to study cells in groups, not individually.

Dielectrophoresis

Dielectrophoresis relates to the physical phenomenon whereby dielectric particles subject to spatially non-uniform d.c. and/or a.c. electric fields undergo a net force directed toward those regions of space characterized by increasing (pDEP) or decreasing (nDEP) field strength. If the strength of the resulting forces is comparable to the force of gravity, it is possible in essence to create an equilibrium of forces enabling the levitation of small particles. The strength, direction and orientation of the dielectrophoretic force are heavily dependent on the dielectric and conductive properties of the body and of the medium in which it is immersed, and these properties in turn vary with frequency.

Studies analyzing the effects of dielectrophoretic forces on microorganisms or biological matter generally (cells, bacteria, viruses, DNA, etc.), and on inorganic matter, have suggested for some time the notion of exploiting these forces as a means of selecting a particular body from a sample containing a plurality of microorganisms, characterizing the physical properties of microorganisms and in general allowing their manipulation.

By way of example, international patent application WO 00/47322 teaches the manipulation of generic "packages" of substances (liquid, solid or gaseous) utilizing dielectrophoretic forces generated between contiguous electrodes of an addressable array. All the same, the method described in this reference is not suitable for conducting a study of high biological value on cells and more generally on microorganisms or parts thereof (DNA and RNA sequences, plasmids, etc.), since on the one hand the "package" is subject to significant voltages to allow its manipulation by dielectrophoresis, and on the other, subject more generally to friction against the reaction surface bearing the array of electrodes.

The prior art embraces another system based on the creation of three-dimensional cell manipulation cages by constructing micro octupoles (T. Schnelle et al., in Biochimica et Biophysica Acta, 1157:127-140); in this instance the cell material is levitated and therefore unaffected by frictional or other mechanical stresses, particularly in the case where the dimensions of the manipulation systems adopted are comparable with those of the particles being manipulated, thus reducing the order of magnitude of the voltages used to create the necessary field distributions when undesirable effects appear (Washizu & Kurosawa, Trans. Ind. Appl. 26:1165-1172, 1990; Washizu et al., Trans. Ind. Appl. 30:835-843, 1994).

However, the structures proposed in literature encounter problems of embodiment when the dimensions of the projected cage approach those of the actual cells (to the end of trapping a single cell). In this instance, the problem consists of aligning the two structures which, assembled one with another on a micrometric scale, make up the octupole.

This particular problem is solved according to international patent application WO 00/69565, which discloses an apparatus and a method for the manipulation of particles (the term "particles" is used hereinafter to denote dielectrophoretically manipulated elements utilized in experiments, be they biological entities, substances compounded with a delivery agent, or both; which of the three cases is intended will be discernible from the context) utilizing closed dielectrophoretic potential cages.

At all events, these latter methods of manipulation based on dielectrophoretic levitation of the material for analysis are limited currently to the separation and/or count of the manipulated particles enabled by recognition of the selfsame particles using suitable sensors of specific type prepared and integrated into the array of electrodes and/or disposed internally or externally of the chamber in which the levitational manipulation takes place. This means that such methods can be used only for particles with intrinsic distinctive characteristics (discriminated on the basis of size, for example) detectable with specific sensors, which must be prepared on a case by case basis.

SUMMARY OF THE INVENTION

The object of the invention is to overcome the various drawbacks encountered in prior art methods as outlined above for the manipulation of cells and more generally of chemical/biological material, to the end that chemical and pharmacological assays of high throughput can be conducted swiftly, efficiently, economically, with precision, and without the need (at least initially) to use animals as guinea pigs.

Chemical/biological material, in particular, here and throughout the specification, means any given "entity" whether consisting in a "compound" or a "compound unit", as defined below, or in a cell.

Here and throughout the specification, the term "compound" is taken to mean any given substance probably capable of pharmaceutical activity, namely potentially trasformant DNA or a chemical substance, as found or if necessary suitably immobilized on the surface of microbeads or microencapsulated in a lipid bilayer or liposome, or in a virus, genetically modified or otherwise, capable of functioning as a vector for genetic material.

Here and throughout the specification, the term "compound unit" is taken to mean a liposome containing a predetermined quantity of a compound, as defined above, or a single vector virus. In the event that chemical substances are used to coat a microbead, "compound unit" is taken to mean a microbead having a predetermined quantity of compound immobilized on its surface.

With the foregoing definitions in mind, a first object of the present invention is to provide a method for conducting tests and assays of high throughput and high biological value on entities consisting in single cells or in compound units, of which the nature may even be unknown a priori, such as will allow of identifying cells or compound units of unknown nature in an initially mixed population and possibly thereafter separating the identified cells and/or compound units from the initial population.

A second object of the invention is to provide a method for conducting tests and assays of high throughput and high biological value on single cells, that will allow of identifying the biological activity on the single cells of one or more selected compounds, possibly delivered by one or more singly identifiable compound units, by monitoring the response of the cell to the administration of such compounds. Preferably, it is also an object of the invention to provide a method of the proposed type for assaying biological activity that will allow one compound at a time to be administered to the cells, preferably employing predetermined and adjustable dosages.

A third object of the invention is to provide a testing device that makes use of dielectrophoretic manipulation and will be suitable for implementing the methods indicated above, allowing the stable levitation of neutral dielectric particles or electrically charged particles (cells or compounds), to the end of verifying and controlling the position of each single cell and compound present in the device.

A further object of the invention, finally, is to provide a simple, swift, effective and reliable method for delivering compounds or compound units to cells or microorganisms. Considering a first aspect of the disclosure, the invention relates to a method of conducting tests and assays of high throughput and high biological value on a sample containing chemical/biological material consisting of unknown entities, characterized in that it comprises the steps of:

(a)—introducing the sample including the unknown entities into a first chamber of a testing device comprising at least one array of first selectively addressable and energizable electrodes and at least one second electrode positioned opposite and facing the first electrodes;

(b)—introducing chemical/biological material into the first chamber of the testing device, consisting of known entities identifiable internally of the testing device and having a presumed affinity with the unknown entities;

(c)—selectively creating closed movable potential cages internally of the first chamber by means of dielectrophoretic force generated by the opposed electrodes and trapping at least a part of the entities within the movable cages;

(d)—moving at least one of the movable cages containing the known entities toward the movable cages containing the unknown entities and causing at least one unknown entity to interact with at least one known entity of at least a first type by bringing about the fusion of at least one pair of movable cages containing the relative entities;

(e)—verifying the creation or otherwise of a stable bond between the at least one unknown entity and the at least one known entity of the first type, to the end of determining whether an affinity exists between the two and consequently identifying the at least one unknown entity.

The unknown entities identified in this manner are preferably counted and separated from the remaining entities and recovered externally of the testing device after being transferred to a second chamber of the testing device.

In this way, and in particular utilizing microbeads as the known entities (functionalized for example with special antibodies or with a ligand), the method according to the invention can be utilized in the field of diagnostics to identify and conceivably to count a given organism in a sample, to separate cells on the basis of the antigenic characteristics, for example as in separating neoplastic cells from normal cells, or to study the cellular response triggered by the binding of a ligand to its specific receptor.

Considering a second aspect of the disclosure, the invention relates to a method of conducting tests and assays of high throughput and high biological value on a plurality of first entities selected from a group including cells, viruses, microorganisms, nucleic acids and combinations of these, and a plurality of second entities consisting in compounds or compound units to be tested for their biological activity on the first entities, characterized in that it comprises the steps of:

(a)—introducing the first and second entities into a first chamber of a testing device comprising at least one array of first selectively addressable and energizable electrodes and at least one second electrode positioned opposite and facing the first electrodes;

(b)—selectively creating closed movable potential cages internally of the first chamber by means of dielectrophoretic force generated by the opposed electrodes and trapping at least a part of the entities within the movable cages;

(c)—moving at least one of the movable cages containing the first entities toward the movable cages containing the second entities and causing at least one first entity to interact with at least one second entity of at least a first type by bringing about the fusion of at least one pair of movable cages containing the relative entities;

(d)—verifying the biological activity of the second entity on the first entity by analyzing the resulting interaction utilizing sensors capable of detecting any evidence in the first entity of at least one of a selected group of effects, namely cytostatic, cytotoxic, mitotic, expression of a marker.

More exactly, the aforementioned cytostatic, cytotoxic and mitotic effects are detected by verifying the presence and/or the changed presence of the first entities in the movable cages created around them and/or in proximity to a plurality of first electrodes positioned immediately adjacent to the movable cages containing the first entities and, prior to the execution of the aforementioned step (c), left vacant or occupied by empty movable cages.

Thus, it becomes possible to conduct many thousands of experiments in parallel internally of the same device. Cells of the same type can be treated with a combination of different compounds, or alternatively a combination of cells can be treated with one compound, or again, a combination of both solutions can be utilized. The number of experiments possible with this method can be increased further by varying the "dosage" of the compounds administered to each single cell, or the quantity of a certain type of compound.

Besides the advantage of high throughput, the method allows experiments to be conducted at high speed thanks to the use of low reaction volumes, that is to say small quantities of compounds, also of buffers and other reagents. In effect, the expedient of positioning the particles by dielectrophoretic levitation has the effect of minimizing manipulation of the liquid using awkward and costly microfluidic systems.

This also has an additional and obvious positive impact on the expense of conducting the experiment, as it is possible to reduce the need for large quantities of compounds that are particularly costly and/or difficult to obtain by synthesis.

In contrast to "traditional" systems for immobilizing cells (based on a chemical bond—specific or otherwise—with a substrate), the arrangement of the cells according to the present invention is achieved by means of dielectrophoretic levitation, so that there is no contact and no binding whatever between the material and the device, and this should guarantee that the physiological response is more natural.

Compared to systems based on multiple chambers (microtiters, etc) a further difference and advantage consists in the fact that cell-compound interactions can all occur in the same chamber of the one device, and in practice simultaneously. This reduces the incidence of errors in analysis occurring with apparatus having separate chambers or wells, since the conditions under which the experiment is performed are characterized by greater uniformity.

The method disclosed also permits of analyzing the response of a single cell and not only that of the statistical mean in a population of homogeneous cells, as occurs in almost all of the methods proposed hitherto. This is made possible by the adoption of integrated optical or capacitive type sensing systems, which permit of dispensing with the cumbersome instruments used traditionally for the purpose in this field (TV camera, microscope), albeit such instruments can equally well be used for the visual monitoring of events occurring internally of the device, or simply if preferred for whatever reason.

In addition, conventional feedback control techniques can be employed, processing the information returned by the sensors integrated into the device, to perform a series of complex operations entirely in automatic mode, such as the selective recovery of certain particles undergoing analysis.

Virtually the entire method can be automated and controlled electronically, rendering it particularly adaptable to varying user requirements. The high level of automation obtainable also limits the incidence of error associated commonly with the repetitive manual operations performed in other screening procedures.

Moreover, the method disclosed can be utilized to deliver not only prospective pharmaceutical compounds, microencapsulated or otherwise, but also opportunely functionalized microbeads.

Such beads can be of dimensions comparable to those of cells or indeed much smaller, and coated by conventional methods for example with antibodies (Ab) or other substances able to interact with cell receptors.

Microbeads coated opportunely with probe DNA (o RNA) can be made to interact with others coated with target DNA (o RNA) as part of a hybridization test, for example to identify the target (molecular diagnostics) or in single nucleotide polymorphism (SNP) analysis.

Considering a third aspect of the disclosure, the invention relates to a multifunctional testing device composed of a first module comprising an array of first electrodes, singly and selectively addressable and energizable at least in part, arranged on an insulating support; a second module comprising at least one second electrode positioned opposite and facing the first electrodes and an upper supporting structure; also a spacer element disposed between the first and the second module and delimiting a liquid or semi-liquid environment during operation, characterized in that the spacer element is embodied in such a manner as to establish at least one first chamber and at least one second chamber internally of the device, interconnected hydraulically by at least one narrow passage and delimiting the liquid or semi-liquid environment, which is thus divided by the at least one narrow passage into at least two partial environments uninfluenced hydraulically one by the another and coinciding with the at least two chambers.

The two chambers are furnished with selectively and controlledly openable orifices functioning as respective inlets and outlets, whilst the array of first electrodes functions as the bottom of the chambers and of the at least one narrow passage allowing communication between the chambers.

With this solution, it becomes possible to perform tests and operations in numbers that could not be handled hitherto by a single testing device, executed swiftly and reliably, with ease and at low cost (given that the procedures can all be implemented without difficulty by electronic programming). In effect, the prior art solutions proposed thus far in the field of combinatorial chemistry betray sundry problems, many of which can be overcome with the device according to the invention by virtue of its ability to create a spatial distribution of particles, or more simply to control their position, employing a targeted distribution of electrical fields designed to create closed potential cages by means of dielectrophoretic force. These cages can be manipulated in such a way that a particle trapped internally of a corresponding cage is made to cover appreciable distances internally of the device.

Finally, the invention relates to a method of delivering first entities consisting in compounds or compound units, to second entities, characterized in that it comprises the steps of:

(a)—introducing the first and second entities into a chamber of a testing device comprising at least one array of first selectively addressable and energizable electrodes and at least one second electrode positioned opposite and facing the first electrodes;

(b)—selectively creating closed movable potential cages internally of the chamber through the agency of dielectrophoretic force generated by the opposed electrodes and trapping at least a part of the entities within the movable cages;

(c)—identifying and selecting the cages containing first entities;

(d)—moving at least one of the movable cages containing the first entities toward the movable cages containing the second entities;

(e)—causing at least one movable cage containing a first entity to fuse with a movable cage containing a second entity.

The method thus affords the facility of bringing selected substances into contact with other selected substances or organisms in a controlled manner, swiftly and effectively, not only for the purpose of conducting tests but also of inducing changes or reactions intentionally while keeping the products of reaction "within boundaries", for example producing genetic alterations in microorganisms that can be easily recovered subsequently.

BRIEF DESCRIPTION OF THE DRAWINGS

Other features and advantages of the invention will emerge more clearly from the following description of certain preferred embodiments illustrated by way of example, and implying no limitation, with the aid of the accompanying drawings.

BEST MODE FOR CARRYING OUT THE INVENTION

Figure 1:
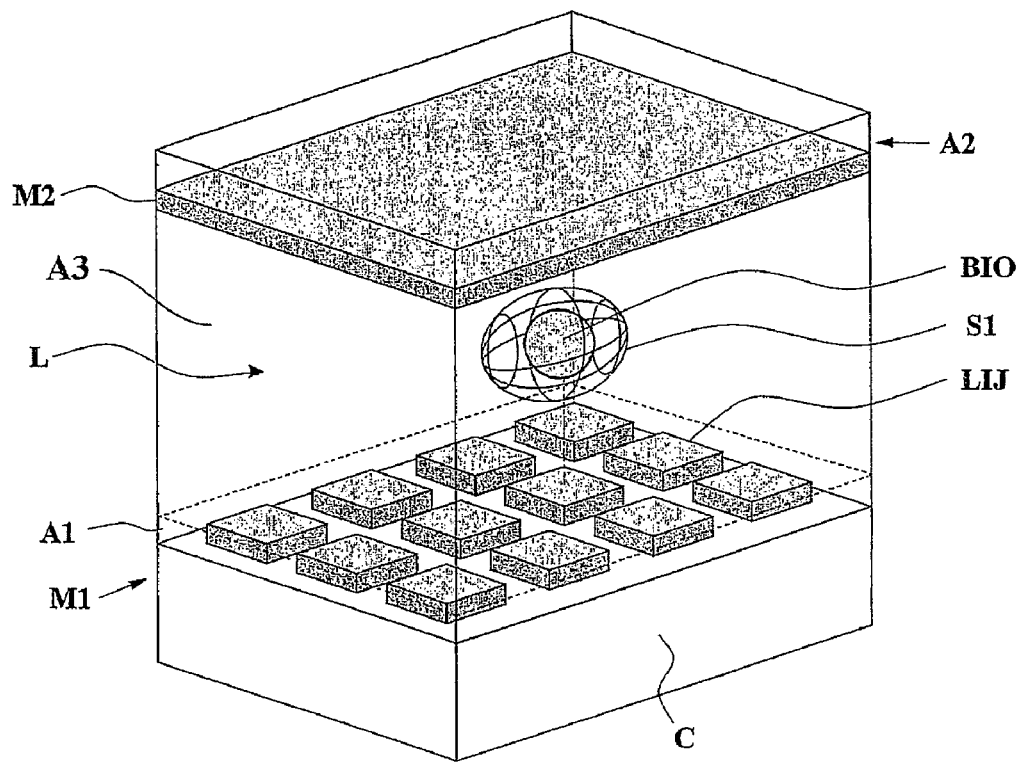
FIG. 1 illustrates part of a conventional device for the manipulation of samples by dielectrophoresis, viewed schematically and in perspective.
Figure 2:
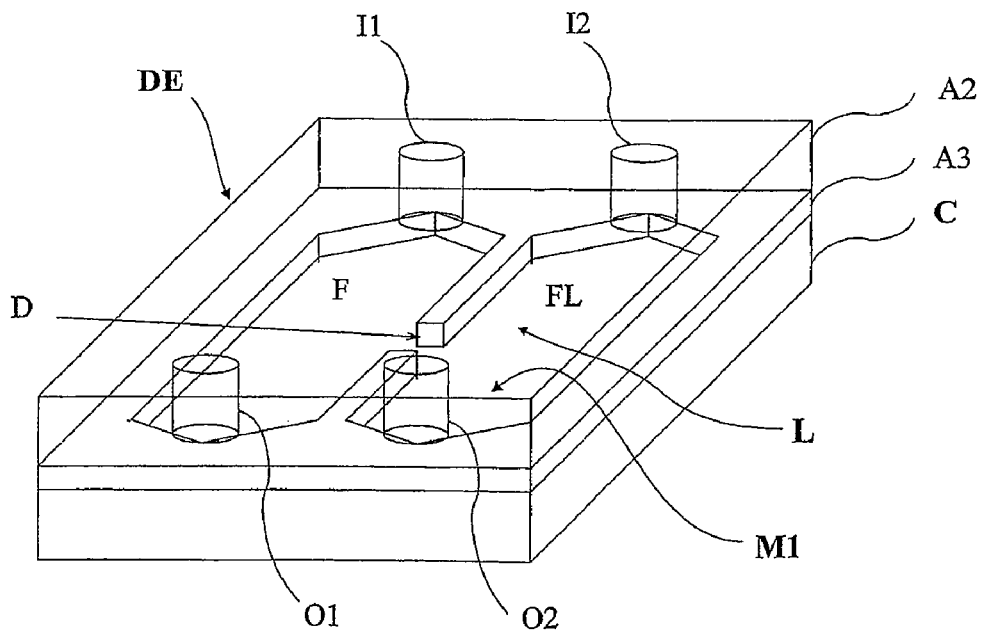
FIG. 2 is a schematic three-dimensional view of the device embodied in accordance with the present invention.

With reference to FIGS. 1 and 2, the present invention is based on the use of a testing device embodying a technology disclosed in international patent application WO 00/69565, filed by the same applicant, of which the content is imported here insofar as it provides a useful reference for the purposes of the present disclosure; in effect, the device described herein incorporates new and original structural features not mentioned in the aforementioned application, designed especially in such a way that the test and assay methods according to the present invention can be performed simply, efficiently, economically and with a rational use of space.

The proposed device, illustrated schematically in FIG. 1, comprises two main modules, of which a first consists in a array M1 of electrodes LIJ arranged in orderly rank and file on an insulating support structure A1. The electrodes LIJ can be fashioned from any given conductive material, selected preferably from the metals compatible with the technology of electronic integration, whilst the insulating medium of the support structure A1 might be silicon oxide or indeed any other insulating material.

The form of the electrodes LIJ making up the array M1 can be selected from a number of types, in FIG. 1 the electrodes LIJ are square, albeit this implies no limitation. Each element of the array M1 consists in a single electrode LIJ serving to generate a dielectrophoretic cage S1 by means of which to manipulate a biological sample BIO internally of a liquid or semi-liquid environment L delimited by a spacer element A3.

A region C beneath the electrodes serves to accommodate integrated sensing circuits that might be incorporated into the device, that is to say sensors of conventional embodiment (not illustrated for the sake of simplicity), selected from a number of types, such as will detect the presence of an entity to be manipulated internally of the potential cages S1 generated by the electrodes. In a preferred embodiment of the device, the second main module consists substantially of a single large electrode M2, covering the device in its entirety. Finally, the device may also include an upper support structure A2, functioning as a lid for the device and enclosing the liquid or semi-liquid environment L.

The simplest form for the second electrode M2 is that of a plain flat and uniform surface; other forms of greater or lesser complexity are possible (for example a grid of given mesh size through which light is able to pass). The most suitable material for the upper electrode M2 will be a transparent conductive material deposited on a support structure A2 of glass. Besides allowing the inclusion of sensing circuits as outlined previously, this solution will also enable the use of traditional optical inspection means (microscope and TV camera) located above the device.

The schematic diagram of FIG. 2 represents a device DE embodied in accordance with the invention and derived from the device of FIG. 1, and accordingly, such details as appear similar or identical in the two drawings are indicated for the sake of simplicity using the same references.

The device DE comprises an upper module A2 supporting a single electrode M2 (not indicated in the interests of simplicity), a lower module C carrying a array M1 of selectively addressable and energizable electrodes LIJ (not illustrated), also a spacer A3 interposed between the two main modules A2 and C and encompassing a liquid or semi-liquid environment L which in operation will consist of suitable buffer solutions. In this instance however, according to the invention, the spacer A3 is fashioned in such a manner as to create two internal chambers F and FL, interconnected hydraulically by way of at least one narrow passage D and delimiting the environment L, which is thus divided by the narrow passage D into two partial environments uninfluenced hydraulically one by the other and coinciding with the two chambers F and FL. Each chamber F and FL is equipped further with selectively and controlledly openable orifices functioning as inlets and outlets, denoted I1 and O1 (chamber F) and I2 and O2 (chamber FL) respectively; the array M1 of electrodes LIJ functions as the bottom of both chambers F and FL and of the interconnecting narrow passage D.

The device thus embodied is utilized, according to the invention, in the manner now to be described.

High Throughput Screening

In the method according to the present invention, the experimenter can introduce the sample (be it cells, microencapsulated prospective pharmaceutical compounds or functionalized microbeads) through the relative inlet I1 (FIG. 2) and into the manipulation environment, using conventional instruments familiar to a person skilled in the art (peristaltic pumps, pipettors, Hamilton syringes, etc.), employing a procedure that can be entirely automatic, or proceeding manually, according to requirements. The sample is subject to a dielectrophoretic force of suitable strength, in such a manner as to trap it within minimum of potential and cause it to travel greater or lesser distances internally of the device. Before these operations can commence, in any event, the chambers F and FL (FIG. 2) of the device must be filled with a suitable buffer solution by way of the orifices I1 and I2. During this step, the orifices O1 e O2 on the opposite side of the chambers are left open to avoid the formation of air bubbles that would prevent the device DE from functioning correctly.

The fact of being able to displace levitating particles through the sole force of dielectrophoresis is instrumental in minimizing the manipulation of the liquid using awkward and costly fluidodynamic systems (microfluidics). The selected particles can be gathered in the inlet area F (where there is high flow transitorily and possible turbulence), then directed through the narrow passage D in the central separator and into the normally flowless adjacent chamber FL, moving the particles rather than the liquid and thus avoiding stress through friction and contact. In this way the particles can be arranged in an orderly matrix or more simply allowed to maintain the position assumed spontaneously within the chamber.

Having generated and/or maintained the required placement, it is then possible to displace other particles, be they cells or compounds to be assayed, and bring them into contact with those to be analyzed.

It is therefore possible to conduct thousands of parallel experiments internally of the same device. Cells of the same type can be treated with a combination of different compounds, or alternatively a combination of cells can be treated with one compound. It is also possible to treat different cells with different compounds in the course of one experiment. The number of experiments possible with this method can be increased further by varying the "dosage" of the compounds administered to each single cell, i.e. the number of units of a certain type of compound, or even administering different compounds in succession to each single cell.

This is illustrated by the following formula:

$$N_E = n°2^{(c°p)}$$

Where NE is the number of single experiments that can be conducted within the overall experiment, n is the number of different cells utilized, c the number of different compounds utilized, and p the dosage of the compounds.

Methods of Delivering Substances

The manner in which substances to be administered are delivered to the cells of interest will depend first and foremost on where the action is to take place, in other words whether the substance is to enter the cell or whether it can interact with a receptor externally of the cell, as well as on the chemical and physical properties of the substance being tested.

Substances that Must Enter the Cell

In cases where the substance must be introduced into the cell to perform its hypothetical activity, the methods of delivery will change significantly according to the chemical and physical properties of the selfsame substance:

Substances that do NOT require microencapsulation.

This category comprises all those substances naturally capable of passing though cell boundaries (membrane, and wall if any), in other words broadly apolar substances that generally form a separate phase in aqueous solutions (with the exception of certain polar substances that are imported spontaneously into the cell by membrane transporter proteins). For many of these apolar substances it is sufficient to produce emulsions, using prior art methods, in which the diameter of the beads of substance in the emulsion are compatible with the dimensions of the dielectrophoretic cages in which they will be manipulated. Others (e.g. retinoic acids) are delivered by a liposome, intercalated with phospholipids as constituents of the lipid layer of the liposome.

Substances that require microencapsulation.

This category takes in all polar substances that must enter the cell to perform their action but which dissolve in aqueous solutions (including nucleic acids). To enter the cell, these substances need to be microencapsulated, for example embedded in a bilayer of phospholipid (liposome). Fusing with the wall of the target cell, the liposome can deliver its content into the cytoplasm. It is also possible to use special microbeads impregnated with the substance of interest, which are absorbed by the cell.

Alternatively, as in the case of nucleic acids, for example, substances can be vectored by viruses, genetically modified as appropriate by conventional methods. Whilst viruses are significantly smaller than cells, the expedient of manipulating them by dielectrophoresis nonetheless falls within the scope of the prior art in this field.

Substances that Must not Enter the Cell

This category includes all those substances of which the action corresponds to that of a receptor-ligand mechanism. Unless these happen to be small molecules soluble in the selected buffer, they must be delivered with the aid of microbeads, that is to say coating microbeads of suitable material with these same substances. Other types of molecules can also be delivered on the surface of liposomes. Finally, other cells can themselves deliver the ligand.

Strategies for Ordering Cells and Compounds

In order to conduct experiments employing the method disclosed, the experimenter must necessarily be able to know the position and type of each cell and/or compound utilized.

Strategies for ordering the cells and compounds fall essentially into two categories:

Sequential introduction

Figure 3:
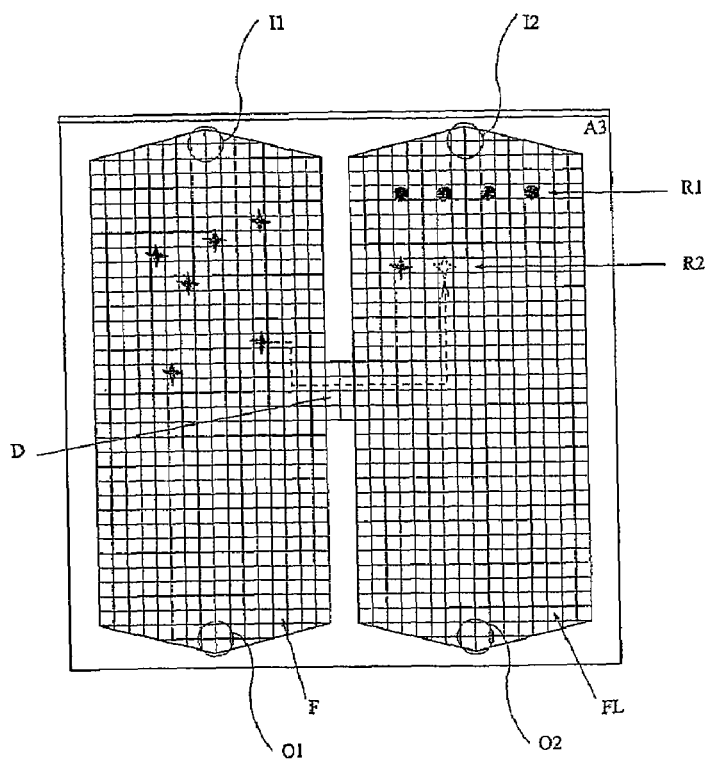
FIG. 3 is a schematic illustration showing one of the possible ordering strategies that might be utilized in the method according to invention, consisting in introduction and placement implemented sequentially for the different types of cells.

One possible procedure is to introduce the cells and/or compounds into the device in sequence. FIG. 3 shows an example of how cells are ordered sequentially. In this instance the type of cell obviously is known beforehand, and it is sufficient to arrange proximity sensors in alignment with at least one electrode pocket of the device. The cages moving over this pocket can be characterized according to the presence or absence of the particle. If presence is sensed, the particle is placed on the array; if not, the cage can be ignored and the next cage in sequence sensed. The proposed procedure can be implemented using external sensors such as TV cameras connected to a microscope, or alternatively the support structure A1 can incorporate both the electrodes serving to manipulate the biological particles, and the devices serving to sense them. The sensors can be of capacitive or optical type. Once introduced through the inlet I1 (FIG. 3) into the flow chamber F of the device, the biological elements or particles are placed in an orderly arrangement R2 in the flowless chamber FL, where there may already be other cell types R1, introduced and ordered previously and included in the same experiment. If on the other hand all the pockets are equipped with sensors then the situation is simplified. The cages containing particles are identified in the flow chamber F immediately following the introduction of the new species, and moved to the selected positions in the flowless chamber FL.

Surplus particles can be removed by introducing further liquid through the inlet orifice I1 of the flow chamber, thereby flushing the particles from the chamber together with the excess liquid by way of the relative outlet O1.

Discrimination internally of the device

Using Sensors Able to Identify the Type of Cell or Substance

Figure 4:
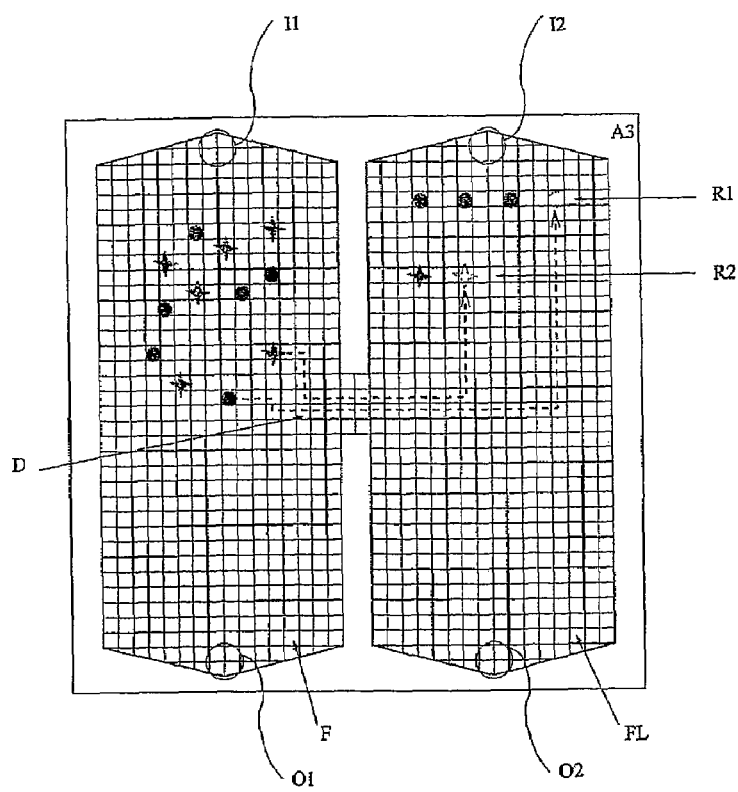
FIG. 4 llustrates an-ordering strategy consisting in the simultaneous introduction of several species and the selective placement of different species.

Rather than introducing cells or compounds in orderly sequence, the facility exists, with a device incorporating sensors able to detect not only the presence but also the type of cell or compound that may be trapped in a cage, of introducing the cells randomly and leaving the device to arrange them automatically (as described in patent PCT/WO 00/69565). Likewise in this instance the procedure is conducted with the aid either of externally located sensors or of optical or capacitive sensors integrated into the device. FIG. 4 shows an example of this solution. The biological particles are introduced by way of the inlet I1 into the first chamber F of the device activating a temporary flow. Here they are identified according to type by the discriminating sensors. Thereafter, each single particle is ordered according to type in the flowless chamber FL together with the others of its kind R1 and R2. A type-discriminating sensor can be located beneath each pocket or even under one pocket only. In the latter instance it will be advantageous to locate the sensor under a pocket near to the passage D between the two chambers, through which the cages will necessarily be directed.

As regards the version of the method involving the use of functionalized microbeads, the problem of ordering the particles included in the test, and more especially of their identification, is facilitated in part by the characteristics of the microbeads. Once the desired arrangement of the cells has been generated and/or maintained utilizing one of the strategies described, the experimenter can simply introduce a mixture of microbeads functionalized with different antibodies into the device, with no need to adopt a sequential procedure. It is sufficient that the substances have homogeneous pairs of physical and immunological characteristics, in other words that each specific type of antibody is matched by different characteristics of the particle by which it is delivered. An example of this is shown in Table 1: three antibodies (specific mAbs) for three different antigens of three different organisms are used to coat three types of particles, differing on the one hand in terms of colour and on the other in terms of dielectric constant.

TABLE 1

Example of pairing between physical and immunological characteristics of functionalized microbeads. Antigenic characteristics can be associated with different physical characteristics of the microbead.

| Physical characteristics of microbead | | |
|---|---|---|
| Colour | Dielectric constant | Type of antibody |
| White | ε1 | S. aureus Ag H |
| Yellow | ε1 | H. influenzae Ag K |
| Green | ε1 | E. coli Ag O |
| White | ε1 | S. aureus Ag H |
| White | ε2 | H. influenzae Ag K |
| White | ε3 | E. coli Ag O |

The number of particles can also be increased by adopting combinations of physical characteristics. An example of this is shown in Table 2.

TABLE 2

Example of pairing between physical and immunological characteristics of functionalized microbeads.

| Physical characteristics of microbead | | |
|---|---|---|
| Colour | Dielectric constant | Type of antibody |
| Yellow | ε1 | Ab1 |
| Yellow | ε2 | Ab2 |
| Green | ε1 | Ab3 |
| Green | ε2 | Ab4 |

Besides colour, other characteristics such as reflectance and possibly fluorescence can be detected easily with the aid of a suitable external sensor. Transparency and difference in dielectric constant can be detected with integrated sensors of optical and capacitive type, respectively.

Similarly, complexes formed by the antigen antibody interaction between cell and beads, identified simply through the match between the physical and immunological characteristics of the microbeads, can at this point be processed further in accordance with the invention, as described in due course. Discrimination on the basis of physical characteristics, using fluorescence in particular, can be used to identify particles consisting not only of functionalized microbeads, but also of liposomes carrying given compounds either internally or on the surface.

With Selective Actuation

It is possible to exploit the way in which the behaviour of particles in the device changes with the variation in frequency of the applied electric fields. As frequency varies, in effect, the cells can undergo a change in direction and/or strength of the net dielectrophoretic force that drives them toward regions of the device with decreasing field strength (nDEP) or toward regions with increasing field strength (pDEP). Different cells have different transition curves depending on their dielectric and conductive properties (their so-called "spectral signatures"). In practice, this phenomenon can be utilized to trap and move a single cell species (as described in patent PCT/WO 00/69565) and thus to separate various species from a mass of organisms. In this case, knowing how the cells will migrate at the selected frequency and having sensors able to detect the presence of the cell, the experimenter introduces a mixture of organisms into the chamber that will then be separated directly by the device. Again, the presence of the sensors can be detected by sensors operating externally or integrated into the device (optical or capacitive).

During the course of these operations, the information returned by the sensors can be used to modify the control and the operations to be performed according to the status of the system, and to change or adjust the programming of the device. It is also possible to generate a virtual representation (graphic, for example) of the status of the system to the end of optimizing the interface between device and user for the purposes of programming and of analyzing results.

Experiments Execution

Experiments with Liposomes, Viruses or Substances Emulsifiable in the Buffer Solution to be Utilized In practice, this type of experiment consists in generating or at all events maintaining an ordered arrangement of cells (or compounds) and causing them to interact with the compounds (or cells) being assayed. This is done simply by causing the dielectrophoretic potential cages containing/conveying the cells and compounds to fuse together. In the case of microemulsified apolar compounds (e.g. steroids or triglycerides), these pass spontaneously through the cell boundaries and are able thus to bring about their action, if any, within the cell. In the case of compounds microencapsulated in liposomes, the phospholipid sac fuses with the cell membrane releasing the compound into the cell where it will produce its action, if any. Where particles are associated with genetically modified viral vectors, the gene of the substance being tested is inserted into the DNA of the virus by a conventional procedure. Through the agency of the particular mechanisms peculiar to it, the virus will introduce the genetic material into the cell where it will then produce its action, if any.

Experiments Using Beads Functionalized with Antibodies

Microbeads functionalized with antibodies are used in all cases where there is a need to discriminate a cell on the basis of characteristic molecules (antigens) exposed on its surface (wall or membrane). Typical instances are diagnostic applications and procedures concerned with the separation of particular populations of cells from others that otherwise could not be distinguished.

Beads functionalized with antibodies can be delivered by means of a dielectrophoretic potential cage to the cell and offered in contact to the cell simply by causing the cage containing the bead to fuse with the cage containing the cell. Among the singular characteristics of the method according to the invention is that it can be used to run a binding check on the antibody and the identified antigen.

The experimenter can seek to detach the cells from the functionalized microbeads, and thus carry out a dependable verification on the strength of the bond between antigen and antibody, adopting one of the following strategies:

Varying the Strength of the Electric Field

At constant frequency, with the cell and the microbeads both exposed to nDEP, the experimenter can check the strength of the binding force between the antibody coating the bead and the antigen present on the surface of the biological particle, verifying the resistance of the antigen-antibody complex to the force of separation when the two particles are attracted into two distinct cages by varying the strength of $\nabla(E_{rms})^2$, i.e. the strength of the dielectrophoretic force, which is:

$$<F> \propto Re[fcm(\omega)]\nabla(E_{rms})^2$$

in other words proportional to $\nabla(E_{rms})^2$. Increasing the voltages to the electrodes, that is to say increasing the amplitude of the voltage applied between the electrodes, it is also possible to increase the strength of the dielectrophoretic force attracting the two particles into distinct cages.

Varying the Frequency of the Electric Field

Figure 5:
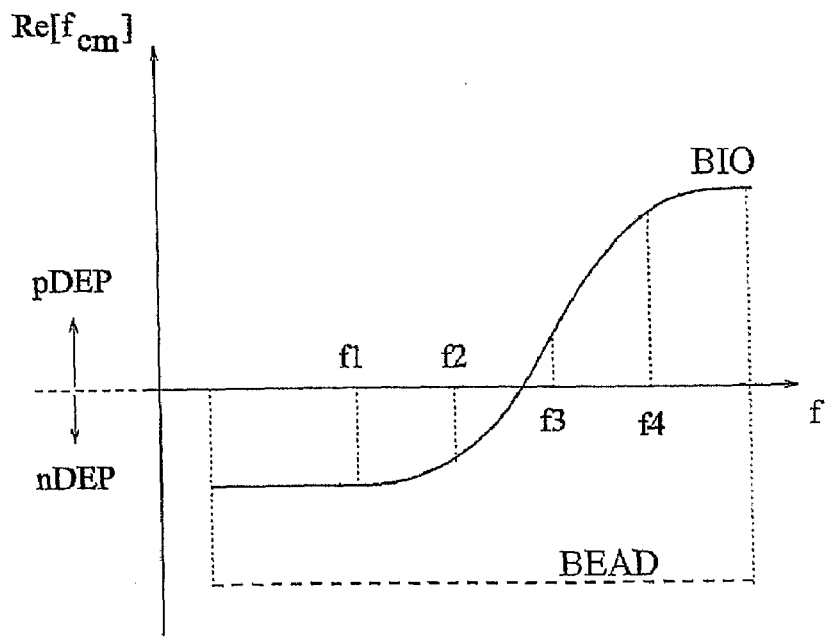
FIG. 5 shows the curve described by dielectrophoretic force in conditions of varying frequency, for cells (BIO) and for microbeads (BEAD)

The frequency response of the dielectrophoretic force (Re [fcm] in FIG. 5) is generally different in microbeads and cells respectively. In effect, varying the frequency has the effect of influencing the force factor $fcm(\omega)$. This has little effect on the microbeads (BEAD in FIG. 5), in respect of which the dielectrophoretic force remains substantially constant in the negative sector (nDEP). In practice the beads continue to be drawn toward the centre of the dielectrophoretic potential cages. For cells, by contrast (BIO in FIG. 5), the dielectrophoretic force changes from negative to positive with the variation in frequency between the electrodes. The effect of this in practice is that the cells tend to be drawn from the centre of the cages toward the electrodes where the electric field is strongest.

Varying Frequency and Strength of the Electric Field Simultaneously

It is also possible to check the match of the bond between antigen and antibody based on the two aforementioned parameters, by varying both the frequency of the electric field, i.e. dielectrophoretic force decreasing (nDEP) or increasing (pDEP), and the strength of the electric field, i.e. the modulus of the dielectrophoretic force field.

EXAMPLES OF CHECKS ON SPECIFICITY OF ANTIGEN-ANTIBODY BOND

The situations that arise depend to a great extent on the dimensions of the microbeads, on the prevailing positive or negative dielectrophoretic force, and on the existence or otherwise of a bond between antigen and antibody:

Separation using nDEP only

The following method is particularly suitable in the event of the beads being of dimensions comparable to those of the particle BIO and of the cage.

Figure 6:
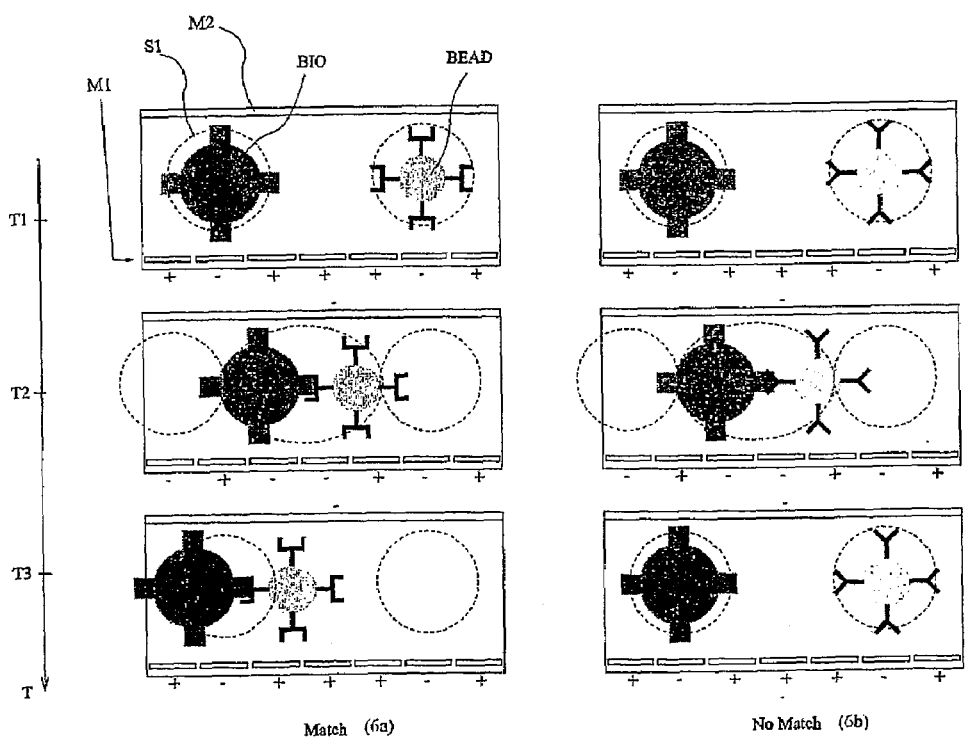
FIG. 6 illustrates the operation of the dielectrophoretic system utilized in accordance with the invention when two cages are fused, one containing a cell for analysis and the other containing a microbead coated with antibodies, of dimensions comparable to those of cell, in the case of a match (6a) and of no match (6b) between antigen e antibody.

Match (Illustrated in FIG. 6a)

Initially (time T1 in FIG. 6a), the cell BIO and the functionalized microbead BEAD occupy two adjacent cages. The cages are indicated schematically by relative phantom lines S1, each indicating the portion of space in which a significant dielectrophoretic force is generated. Next (time T2 in FIG. 6a), a bigger cage is generated as the two particles converge and enter ultimately into physical contact internally of this same cage. In the case of a match, the antibodies on the microbead recognize their specific antigen and bind to it. Thereafter (time T3 in FIG. 6a), the initial cages are reinstated but the microbead remains anchored to the cell by reason of the antigen-antibody bond and the two continue to occupy the one cage.

No Match (Illustrated in FIG. 6b)

Initially (time T1 in FIG. 6b,) the cell and the functionalized microbead occupy two adjacent cages. Next (time T2 in FIG. 6b), a bigger cage is generated as the two particles converge and enter ultimately into physical contact internally of this same cage. However, if there is no match, the antibodies on the microbead do not recognize any specific antigen and consequently will not bind to the cell. Thereafter (time T3 in FIG. 6b), the initial cages are reinstated and the microbead and cell reoccupy their original positions.

Separation using nDEP and pDEP

The following method is suitable in the event of the beads being either of dimensions smaller than those of the cell BIO or of dimensions comparable to those of the cell BIO.

Match with Prevailing Positive Force on Microbead-Cell Complex

Initially (time T1 /Match & prevailing pDEP in FIG. 7a), the cell BIO and a number of functionalized microbeads BEAD occupy two adjacent cages. The cages are made to converge by changing the polarity of the electrodes in the array M1 (see FIG. 7a). As a result (time T2 /Match & prevailing pDEP in FIG. 7a), the beads enter into physical contact with the cell and cluster around its surface. In the case of a match, the antibodies on the microbeads recognize their specific antigens and bind to them. A change of frequency is now applied, the effect of which is to subject the cell to the positive dielectrophoretic force and cause the cell-microbeads complex to fall into a zone of maximum potential, or between the electrodes (time T3 /Match & prevailing pDEP in FIG. 7a). The cages are manipulated in an attempt to separate the cell from the beads but these continue to cling to the cell as a result of the antigen-antibody binding force (time T4 /Match & prevailing pDEP in FIG. 7a). Thereafter, the situation is assessed by verifying the presence of particles in the neighbourhood of electrode L100 and the absence of particles in the neighbourhood of electrode L200 time T5 /Match & prevailing pDEP in FIG. 7a). This can be accomplished utilizing optical sensors (integrated or otherwise) or capacitive sensors.

Match with Prevailing Negative Force on Microbead-Cell Complex

Figure 7:
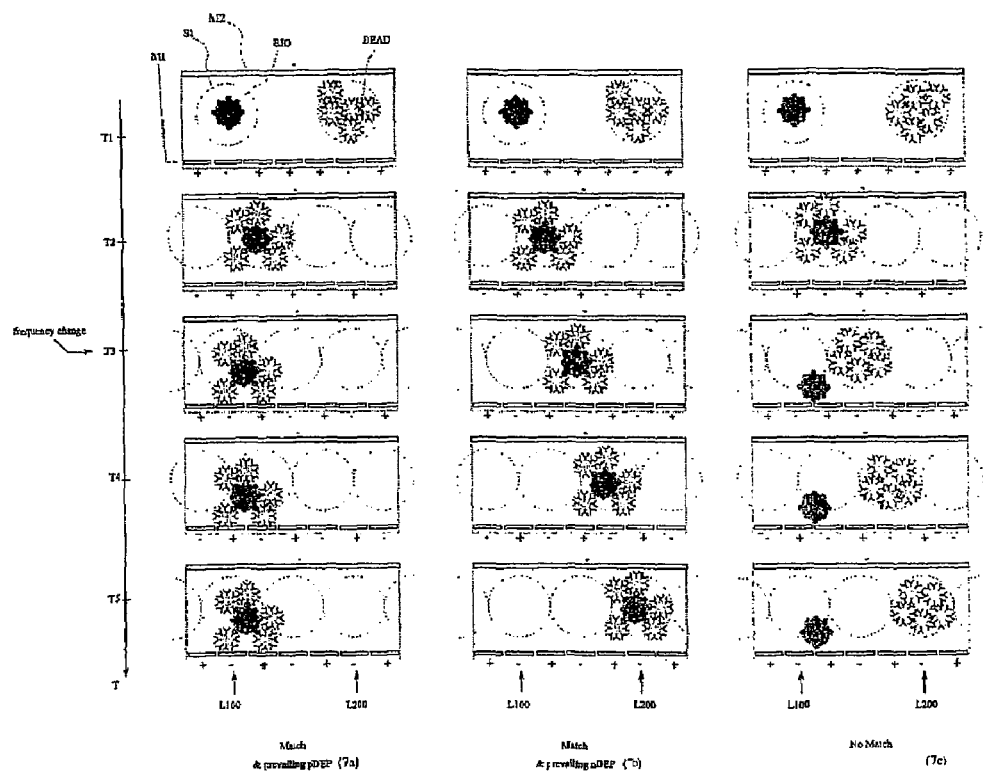
FIG. 7 illustrates the operation of the dielectrophoretic system utilized in accordance with the invention when two cages are fused, one containing a cell for analysis and the other containing microbeads coated with antibodies, of dimensions less than those of the cell, in the case of a match between antigen and antibody with a prevailing positive dielectrophoretic force (7a), a match but with a prevailing negative dielectrophoretic force (7b), and no match (7c)

The situation during the initial steps (times T1-T3 in FIG. 7b) is the same as described above, with the cell BIO and a number of functionalized microbeads BEAD occupying two adjacent cages (time T1 /Match & prevailing nDEP in FIG. 7b). Likewise in this instance the cages are made to converge by changing the polarity of the electrodes in the array M1, and the microbeads enter into physical contact with the cell, clustering around its surface (time T2 /Match & prevailing nDEP in FIG. 7b). This again is an example of a match, with the antibodies present on the microbeads recognizing their specific antigens and binding to them. A change of frequency is applied, as a result of which the cell is subject to the positive dielectrophoretic force, but given the prevailing nDEP on the microbeads, the cell-microbeads complex is maintained in levitation (time T3 /Match & prevailing nDEP in 7b). The cages are manipulated further in an attempt to separate the cell from the beads but the cells continue to cling to the beads as a result of the antigen-antibody binding force (time T4/Match & prevailing nDEP in FIG. 7b) so that the complex moves as a single entity within the one cage as the variation in polarity of the electrodes dictate. Finally, the situation is assessed by verifying the absence of particles in the neighbourhood of electrode L100 and the presence of particles in the neighbourhood of electrode L200 (time T5 /Match & prevailing pDEP in FIG. 7b).

No Match

Initially (time T1 /No Match in FIG. 7c), the cell BIO and a number of functionalized microbeads BEAD occupy two adjacent cages. The cages are made to converge by changing the polarity of the electrodes in the array M1. The microbeads now enter into physical contact with the cell and cluster around its surface (time T2 /No Match in FIG. 7c). In this instance the antibodies on the microbeads do not recognize any specific antigen. A change of frequency is now applied, as a result of which the microbeads stay in levitation internally of a cage whereas the cell drops toward the electrodes, being subject to pDEP (time T3 /No Match in FIG. 7c). The cages move further, the cell remains near the electrodes, whilst the microbeads shift from cage to cage (time T4 /No Match in FIG. 7c). Finally, the situation is assessed by verifying the presence of particles in the neighbourhood both of electrode L100 and of electrode L200 (time T5 /No Match in FIG. 7c).

Observation of Cell Response

Besides the facility of checking each single cell to the end of conducting a variety of experiments, the methods according to the present invention afford the advantage that the physiological response of cells can be analyzed directly, without having to recover them from the testing device.

It remains possible nonetheless, given the features of the device, to recover the cells of interest without undue difficulty in the event that it is wished to carry out further experiments on them. Once the flow chamber F of the device has been flushed clear of any residual particles with buffer solution, the cells of interest can be returned from the flowless chamber FL to the flow chamber F and removed by pumping through more buffer solution.

The proposed method allows the experimenter essentially to analyze the response of each single cell to the compound, whereas other methods generally allow analysis of the response only in terms of a mean value reflecting a homogeneous population of cells.

The effects generated by the compound are broadly classifiable under four types:
  cytostatic: compound produces a delay in the time taken for cell division to come about;
  cytotoxic: compound induces cell death mechanisms leading ultimately to cell lysis;
  mitotic: compound stimulates cell mitosis (cell division), or a reduction in the time taken for a cell to generate;
  complex: a multifactorial physiological response (induction of second messengers, activation of one or more genes, etc.) of which the effects may not easily be observed but may ultimately coincide nonetheless with one of the foregoing.

Cytotoxic, cytostatic and mitotic effects can be observed with the aid of external optical sensors or integrated sensors. Such sensors might be of the capacitive type, that is, consisting of a circuit able to detect small differences in capacitance between two electrodes of the array; the presence or absence of the cell, or equally its possible lysis or duplication, will alter the value of the capacitance, allowing the experimenter not only to detect the cell but also to determine the number of cells present. Optical sensing likewise can be utilized, in which case the factor enabling discrimination between the presence and absence or the lysis and duplication of the cell is the quantity of photons reaching a sensor positioned beneath a minimum of potential. If a cell becomes trapped in such a minimum, or void, beneath which a sensor is located, the photons incident on the sensor will be fewer to the extent that the cell is less transparent than the liquid in which it is suspended.

In the case of a mitotic effect, one (or more) of the cells generated cannot be contained in the same cage as the parent cell and falls consequently into an adjacent cage, left free for the purpose, where it can be detected by the sensor positioned below this same cage.

Figure 8:
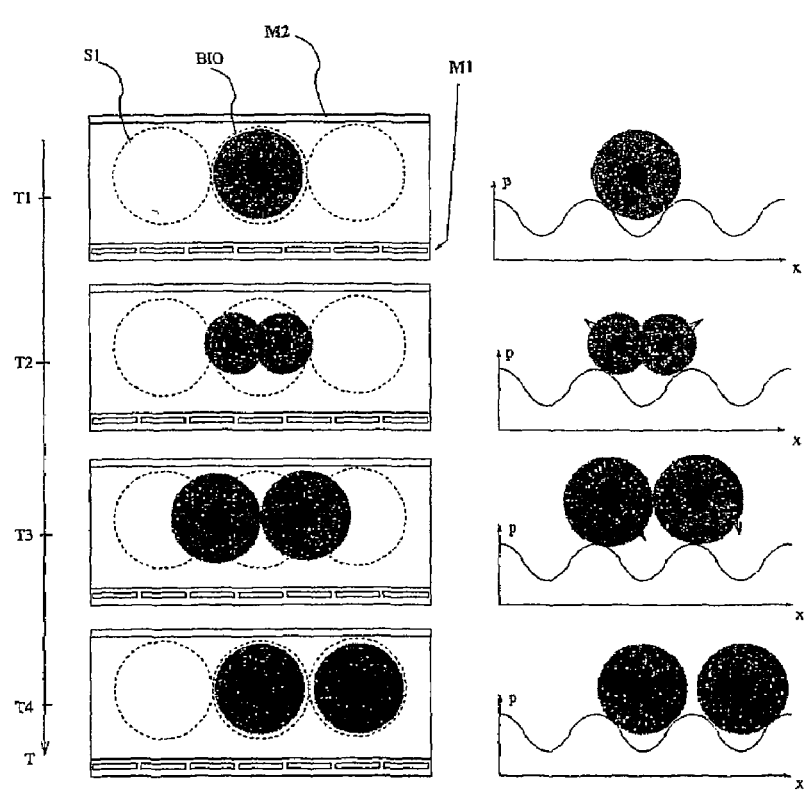
FIG. 8 includes a graph showing a number of minima of potential, and illustrates the displacement of a newly generated cell from the minimum occupied by the parent cell to the adjacent minimum.

FIG. 8 illustrates the above sequence of events, shown in a schematic representation of the device and in a graph indicating the spatial variation of the dielectrophoretic force from one moment to the next.

More exactly, a cell BIO that may or may not have just received a compound occupies a cage S1, or rather a minimal portion of the dielectrophoretic field generated by the device (time T1 in FIG. 8); whether stimulated by the effect of the compound or benefiting from its absence, the cell begins to divide. As long as the two new cells remain connected they do not escape from the cage (time T2 in FIG. 8); with mitosis accomplished, the two cells generated will be caught momentarily between two cages, in effect on the cusps of two due adjacent minima of potential, into which they will inevitably drop (time T3 in FIG. 8); once the cells have effectively divided, the system reaches a new minimum potential energy when each cell has occupied a relative cage (time T4 in FIG. 8). By monitoring the number of cages occupied it becomes possible, utilizing the present method, to identify the accomplished mitosis. Alternatively, use might be made of a capacitive sensor that produces an analog response proportional to the number of cells generated and therefore such as will allow the cells to be counted even when trapped within the same cage.

To analyze different physiological cell responses and complexes induced by a compound, or non macroscopic effects or effects that are not easily identifiable, the preferred method is to use genetically modified cells containing a reporter gene at a selected point of the metabolic pathways that could be influenced by the compound, or a gene that expresses a readily observable protein, typically fluorescent, such as green fluorescent protein (GFP), in place of (or together with, for example in the case of a fusion protein) the normal but not readily observable gene product. This is a technique by now commonplace and utilized by persons with ordinary skill in the art field of microbiology.

Again in this instance the sensors can be integrated or external, but obviously must be of optical type only.

The possibility of analyzing physiological responses, complex or otherwise, is facilitated by the fact that a constant selected temperature can be maintained internally of the device, and similarly by the freedom to utilize different buffers which besides having the right dielectrophoretic characteristics will also include substances that can be metabolized or otherwise by the cells and which thus enable the cells to survive in physiological conditions internally of the device for as long as is necessary to obtain a response.

Applications
  With substances transported or otherwise by liposomes
  Basic research The chief application of this method is obviously that of basic research, where the possibility of checking interactions relative to a single cell opens up completely new fields for experimentation, in particular if the liposome carries a receptor-specific ligand on its surface. Another advantage in terms of basic research is that liposome-liposome interactions can be observed: if one liposome carries a ligand on its surface, with the other liposome carrying the receptor and other proteins known to mediate the signal response, it becomes possible to reconstruct a minimum cell signalling system.

Combinatorial chemistry

The method finds application to advantage in the field of combinatorial chemistry where experimenters must screen libraries of compounds comprising thousands of substances to verify their effect on cells of various types, seeking at the same time to limit both the time and the quantities of substances employed in conducting the test. In this instance the liposome fuses with the cell and releases its content into the cytoplasm. It is also possible to bring about the fusion of two liposomes containing reagents to the end of obtaining a given compound. Finally, interactions between liposomes and porous microbeads can be used to transport a variety of liposomes into the pores of the microbeads.

With substances delivered using microbeads

Among the applications for the method using substances able to functionalize microbeads of various types, in addition to those possible with liposomes, others include:

Diagnostics

The method can be used to identify an organism in a biological sample utilizing microbeads functionalized with antibodies, for example monoclonal antibodies, to locate a specific antigen of the organism. The main advantages of this method over other immunological methods are in particular the high degree of specificity guaranteed by the binding check, the facility of using notably small quantities both of the antibody and of the sample being tested, and, not least important, the high speed of execution afforded by the procedure thanks to its simplicity and to the level of automation incorporated.

Figure 9:
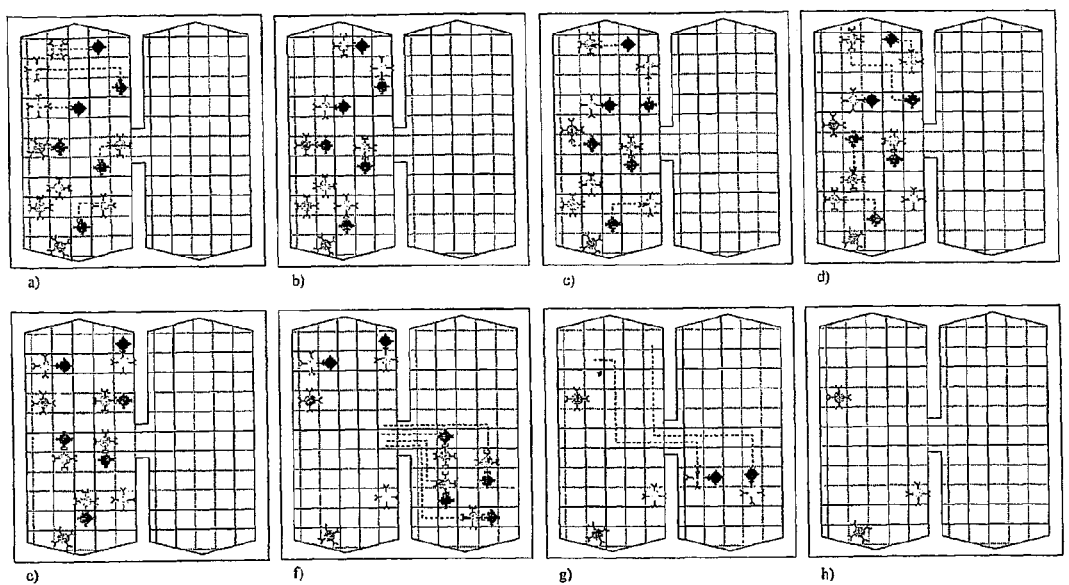
FIG. 9 illustrates the steps of analyzing and selecting specific cells utilizing microbeads functionalized with specific antibodies.

One of the possible applications for diagnostic purposes is shown in FIG. 9, which provides a schematic illustration both of the manner of conducting the diagnostic test and of the procedure for effecting a specific separation of cells (described in due course), given that the initial steps are the same in each case. The procedure can be characterized broadly as follows: the biological sample containing the type or types of cells of interest is mixed with one, or (should the cell types to be identified/recovered be more than one in number), possibly more types of microbead functionalized with antibodies specific to the type or types of cells of interest. The different types of microbeads must be easily identifiable on the basis of their physical characteristics. At this point the mixture is introduced into one of the chambers of the device.

Alternatively, the microbeads can be introduced into the device separately from the sample, proceeding sequentially should it not be possible to discriminate between the different types of microbeads internally of the device.

Cells and microbeads that may not have come into contact when mixed are brought together by an initial dielectrophoretic manipulation step (FIGS. 9a and 9b). Attempts are now made to separate the cells from the microbeads (FIG. 9c). Where complexes cannot be separated, it is assumed that the antibodies fixed to the microbeads have been bound to the antigens on the cells, and these are identified accordingly. Separated cells are then paired with microbeads of a different type to those with which they were in contact before (FIGS. 9d and 9e). The operation is repeated until all the cells of interest have been identified and if possible enumerated.

An application for the method in the field of molecular diagnostics involves the use of microbeads, recognizable either by virtue of being known before their introduction into the device or simply in that they are identifiable internally of the device on the basis of their physical characteristics, which are suitably coated with probe DNA (or RNA) and caused to interact through the agency of dielectrophoretic manipulation with others having a coat of target DNA (or RNA). This method can be used in conducting a hybridization test by homology to identify the target DNA (or RNA), and without utilizing radioactive or fluorescent material in the probe, as required by contrast in conventional methods. Moreover the stringency of the experimental conditions is easily controlled, and varied if necessary, by electronic means (i.e. seeking to separate the microbeads) and in real time, in other words without having to repeat the entire procedure. This is particularly advantageous for example in locating single nucleotide polymorphisms (SNPs) typical of certain serious diseases.

Specific separation of cells

One of the applications of greatest interest for the present invention is that of cell sorting, and more exactly the use of microbeads functionalized with antibodies in enabling the selection of a homogeneous sub-population of cells from a heterogeneous mass.

In effect, the characteristics of the method are such as to ensure a high specificity of recognition, allowing the discrimination of cells that differ even minimally, and above all enabling their separation and recovery from others simply and with negligible risk of contamination from the unwanted part of the cell population. This application is of particular interest in the medical field of oncology.

The procedure can be characterized broadly as follows: the biological sample containing the type or types of cells of interest is mixed with one, or (should the cell types to be recovered be more than one in number), possibly more types of microbead functionalized with antibodies specific to the type or types of cells of interest. The different types of microbeads must be easily identifiable on the basis of their physical characteristics. At this point the mixture is introduced into one of the chambers of the device.

Alternatively, the microbeads can be introduced into the device separately from the sample, proceeding sequentially should it not be possible to discriminate between the different types of microbeads internally of the device.

Cells and microbeads that may not have come into contact when mixed are brought together by an initial dielectrophoretic manipulation step (FIGS. 9a and 9b). Attempts are now made to separate the cells from the microbeads (FIG. 9c). Where complexes cannot be separated, it is assumed that the antibodies fixed to the microbeads have been bound to the antigens on the cells, and these are identified accordingly. Separated cells are then paired with microbeads of a different type to those with which they were in contact before (FIGS. 9d and 9e). The operation is repeated until all the cells of interest have been identified. Cells still bound to microbeads are moved sequentially into the second chamber of the device in homogeneous groups and recovered by flushing out in buffer solution (FIGS. 9f and 9g). Alternatively, stable complexes of the same type are moved into the second chamber of the device, whereupon a force of separation is applied by varying the strength and/or the frequency of the electric field between selected electrodes, sufficient to detach the microbeads from the cells so that they can be reutilized in the first chamber. The cells are recovered from the device by flushing out in buffer solution.

Study of complex responses triggered by receptor-ligand interaction

Using microbeads, the method can be used to study the cell response triggered by the binding of a ligand to its specific receptor. The microbeads, in effect, can also be functionalized with substances other than antibodies, which while capable similarly of binding to a receptor (transitorily to a greater or lesser degree) also trigger physiological responses in the cell. Many cell responses are in fact mediated by interactions of this type in which a substance functioning as a messenger, but unable to enter the cell, encounters a specific receptor that transmits the signal through the cell boundaries, without necessary taking the substance through with it. Messengers generally activate a cascade of information that will ultimately produce one of the four effects described previously: cytostatic, cytotoxic, mitotic and complex.

Given the facility of functionalizing microbeads with the types of substances described, the range of phenomena that can be studied with the method disclosed can be expanded to take in all those substances, in effect the majority among those of interest, which either cannot or should not pass through the cell boundaries yet are able nonetheless to affect the physiology of the cell significantly.

Finally, functionalized microbeads can be utilized in basic research, for example causing them to interact with liposomes: if a microbead carries a ligand on its surface, and a liposome the receptor and the other proteins by which the response to the signal is mediated, it becomes possible to reconstruct a minimum cell signalling system. Microbeads can also be used as vector for the introduction of compounds or compound units into cells or into a compartmentalized environment, for example isolated internally of a liposome; in effect, a functionalized microbead can be internalized by a cell with which it is brought into contact; the same is true in the case of a liposome.

In the event that the objective is to introduce a compound or a compound unit into a cell (or liposome) this same compound or a compound unit can be carried directly by a microbead or a liposome, or conceivably on the surface of another cell, or contained in a vector (a virus, for example, if the compound is a fragment of DNA/RNA) designed to penetrate internally of a cell or liposome when brought into physical contact with these, and the vector itself might also be carried by cells and/or microbeads and/or liposomes.

The invention claimed is:

1. A method of conducting tests and assays of high throughput and high biological value on a sample containing chemical/biological material consisting of unknown entities characterized in that it comprises the steps of:
   (a)—introducing the sample including said unknown entities into a first chamber of a testing device comprising at least one array of first selectively addressable and energizable electrodes and at least one second electrode positioned opposite and facing the first electrodes;
   (b)—introducing chemical/biological material into a first chamber of said testing device, consisting of known entities identifiable internally of said testing device and having a presumed affinity with the unknown entities;
   (c)—selectively creating closed movable dielectrophoretic potential first and second cages within said first chamber generated by said first electrodes and second electrode and trapping at least a part of said unknown entities within the first moving cages and at least a part of said known entities within the second moving cages;
   (d)—moving at least one of said second movable cages containing the known entities toward said first movable cages containing said unknown entities and causing at least one unknown entity to interact with at least one known entity of at least a first type by bringing about the fusion of at least one first movable cage and one second movable cage containing the relative entities;
   (e)—verifying the creation or otherwise of a stable bond between said at least one unknown entity and said at least one known entity of the first type for determining whether an affinity exists between the two and consequently identifying said at least one unknown entity.

2. A method as in claim 1, wherein the entities introduced into the first chamber of the testing device are known entities of a plurality of different types, identifiable internally of the device, and the moving and verification steps (d) and (e) are repeated for each of said unknown entities not bound stably to a known entity of the first type, selectively causing a known entity of a type different to the first type to interact with each unknown entity until all the types of known entity introduced have been eliminated.

3. A method as in claim 1 comprising the further step, performed before the moving step (d), of identifying the moving cages containing said unknown entities.

4. A method as in claim 3 wherein the identification step is performed with the aid of sensors located internally or externally of said testing device or performed directly on said unknown entities before their introduction into said testing device.

5. A method as in claim 1 wherein said known entities are compound units consisting in microbeads or liposomes carrying a compound selected from a group including at least one antibody for a specific antigen and at least one ligand for a specific receptor and at least one DNA or RNA probe and combinations thereof.

6. A method as in claim 5 wherein said known entities are identified internally of the testing device on the basis of at least one physical characteristic detectable by way of a sensor located internally or externally of said device.

7. A method as in claim 6, wherein said at least one physical characteristic is selected from a group including colour, fluorescence, dielectric constant and combinations thereof.

8. A method as in claim 1 wherein said known entities are introduced into the first chamber of the testing device together with said unknown entities.

9. A method as in claim 8, comprising the steps of creating a mixture of said known entities and said unknown entities externally of said first chamber and thereupon introducing said mixture into the first chamber.

10. A method as in claim 1 wherein said known entities and said unknown entities are introduced into the first chamber separately and sequentially.

11. A method as in claim 10, wherein said known entities are identified internally of the test by moving the movable cages in which they are trapped to predetermined positions corresponding to predetermined said first electrodes of the array and memorizing the selfsame positions.

12. A method as in claim 1 comprising the further step of counting the number of unknown entities identified on the basis of their binding stably to the known entities.

13. A method as in claim 1 comprising the further steps of:
   moving the movable cages in such a way as to transfer only unknown entities bound stably to known entities of a single homogeneous type, and therefore identifiable as being of only a single homogeneous type, into a second chamber of the device communicating with the first chamber by way of a narrow passage;
   flushing the entities occupying said second chamber out of the device;
   repeating the moving and flushing steps for all other homogeneous types of unknown entities identified, in sequence.

14. A method as in claim 13 comprising the further steps, performed internally of said second chamber and prior to the flushing step, of separating the identified unknown entities from said known entities of a single homogeneous type bound stably to them, and returning the separated known entities to the first chamber by means of the said movable cages.

15. A method as in claim 14 wherein said separating step is accomplished through the agency of dielectrophoretic force, varying one of the operating parameters of the testing device, namely the strength of the electric field between selected electrodes, the frequency of the electric field between selected electrodes, and combinations thereof.

16. A method as in claim 1, wherein said verification step (e) is performed by reinstating a pair of movable cages fused previously and establishing by means of sensors located internally or externally of the testing device whether said entities are present in both movable cages of the pair or in one only.

17. A method as in claim 16 wherein the sensors employed are optical or capacitive.

18. A method as in claim 16 comprising the further step of checking the stable binding force between said at least one unknown entity and said at least one known entity accomplished by varying one of the operating parameters of the testing device namely the amplitude of the voltage between selected electrodes, the frequency of the voltage between selected electrodes, and combinations thereof.

19. A method as in claim 1, wherein said unknown entities are selected from a group including cells, viruses, microorganisms, and compound units composed of cells and/or microbeads and/or liposomes bearing target DNA and/or RNA, used in conducting hybridization tests.

20. A method of conducting tests and assays of high throughput and high biological value between a plurality of first entities selected from a group consisting of cells and microorganisms, and a plurality of second entities consisting of compounds or compound units to be tested for their biological activity in respect of said first entities; characterized in that it comprises the steps of:
(a)—introducing said first and said second entities into a first chamber of a testing device comprising at least one array of first selectively addressable and energizable electrodes and at least one second electrode positioned opposite and facing the first electrodes;
(b)—selectively creating closed movable potential cages internally of the first chamber by means of dielectrophoretic force generated by said first electrodes and second electrode and trapping at least a part of the entities within the movable cages;
(c)—moving at least one of movable cages containing the said first entities toward movable cages containing the said second entities and causing at least one first entity to interact with at least one second entity of at least a first type by bringing about the fusion of at least one pair of movable cages containing the relative entities;
(d)—verifying the biological activity of the second entity on the first entity by analyzing the resulting interaction utilizing sensors capable of detecting any evidence in the first entity of at least one of a selected group of effects, namely cytostatic, cytotoxic, mitotic, and expression of a marker.

21. A method as in claim 20 wherein said cytostatic, cytotoxic and mitotic effects are detected by verifying the presence and/or the changed presence of said first entities in the movable cages created around them and/or in proximity to a plurality of first electrodes positioned immediately adjacent to said movable cages that contain the first entities and, prior to the execution of the moving step (c), left vacant or occupied by empty movable cages.

22. A method as in claim 20 wherein said sensors are selected from a group including optical sensors, located internally or externally of the testing device, capacitive sensors, and combinations thereof.

23. A method as in claim 20, comprising the further step of recognizing at least one plurality of entities selected from a group consisting of said first entities and said second entities.

24. A method as in claim 23 wherein the recognition step is conducted before or after said step of introducing the entities into the testing device.

25. A method as in claim 24 wherein said recognition step is conducted by means of sensors selected from a group including optical type sensors located internally or externally of the device, and capacitive type sensors.

26. A method as in claim 25 wherein said recognition step is conducted internally of said device on the basis of the response of the entities of at least one said plurality of entities to the dielectrophoretic force generated internally of the device.

27. A method as in claim 23 comprising the step, conducted prior to the moving and verification steps (c) and (d), of utilizing said movable cages to establish a predetermined spatial distribution within the device of said at least one plurality of entities of at least one identified type.

28. A method as in claim 20, wherein each of the movable cages trapping said plurality of first entities contains at least one single said first entity.

29. A method as in claim 28, wherein at least a part of the first entities is trapped in a movable dielectrophoretic potential cage having associated with it a sensor capable of generating a signal proportional to the number of first entities present in the cage.

30. A method as in claim 20, wherein said marker is a reporter molecule expressed internally of the first entity.

31. A method as in claim 30 wherein said compound units are selected from a group including microbeads, liposomes, and cells carrying a compound designed to activate the expression of said reporter molecule.

32. A method as in claim 31 wherein said compound is introduced into said first entity during the interaction step.

33. A method as in claim 31 wherein said compound activates the expression of said reporter molecule through a ligand-receptor type mechanism of interaction.

34. A multifunctional testing device (DL) composed of a first module (C) comprising an array (M1) of first electrodes (LIJ) singly and selectively addressable and energizable at least in part, arranged on an insulating support (A1); a second module comprising at least one second electrode (M2) positioned opposite and facing the first electrodes (LIJ) and an upper supporting structure (A2); also a spacer element (A3) disposed between the first and the second module and delimiting a liquid or semi-liquid environment (L) during operation, characterized in that the spacer element (A3) is embodied in such a manner as to establish at least one first chamber (F) and at least one second chamber (FL) internally of the device, interconnected hydraulically by at least one narrow passage (D) and delimiting the liquid or semi-liquid environment (L), which is thus divided by the at least one narrow passage (D) into at least two partial environments uninfluenced hydraulically one by the another and coinciding with the at least two chambers (F and FL).

35. A device as in claim 34 wherein the first and second chambers (F and FL) are furnished with selectively and controlledly openable orifices functioning as respective inlets (I1,I2) and outlets (O1,O2), and said array (M1) of first electrodes (LIJ) functions as the bottom of said chambers (F and FL) and of the at least one said narrow passage (D) allowing communication between the chambers.

36. A device as in claim 34, wherein said array (M1) of first electrodes (LIJ) is designed to operate together with said second electrode in generating a plurality of dielectrophoretic cages (S1) by means of which to manipulate a biological sample (BIO).

37. A device as in claim 34 wherein said first module (C) is furnished with at least one integrated sensor positioned beneath or in close proximity to at least one of the first electrodes.

38. A device as in claim 37 wherein said at least one sensor is positioned to coincide with said at least one narrow passage (D).

39. A device as in claim 37 wherein said at least one sensor is of optical or capacitive type.

40. A method of transporting first entities consisting in compounds or compound units into second entities, comprising the steps of:
   (a)—introducing the first and second entities into a chamber of a testing device comprising at least one array of first selectively addressable and energizable electrodes and at least one second electrode positioned opposite and facing the first electrodes;
   (b)—selectively creating closed movable potential cages internally of said chamber by means of dielectrophoretic force generated by said electrodes and trapping at least a part of said first entities within first movable cages and of said second entities within second movable cages;
   (c)—identifying and selecting the cages containing first entities;
   (d)—moving at least one of said movable cages containing the first entities toward said movable cages containing the second entities;
   (e)—causing at least one movable cage containing a first entity to fuse with a movable cage containing a second entity, characterized in that said first and second entities and said step of fusing at least one movable cage containing a first entity with a movable cage containing a second entity are such that the first entities are caused to penetrate into the second entities when brought into physical contact with said second entities.

41. A method as in claim 40, wherein said second entities are selected from a group including cells, microorganisms, liposomes, microbeads and the like, and trapped in movable cages.

42. A method as in claim 41, wherein said second entities consisting in cells or microorganisms are fixed to respective microbeads and/or carried on the surface or internally of liposomes.

43. A method as in claim 40, wherein said first entities consisting in said compounds or said compound units are carried directly by cells and/or microbeads and/or liposomes, or by vector designed to penetrate within said second entities once brought into physical contact with the selfsame second entities, the vector in turn being transportable by cells and/or microbeads and/or liposomes.

* * * * *

UNITED STATES PATENT AND TRADEMARK OFFICE
CERTIFICATE OF CORRECTION

PATENT NO. : 7,699,969 B2  Page 1 of 1
APPLICATION NO. : 10/476467
DATED : April 20, 2010
INVENTOR(S) : Nicolo Manaresi et al.

It is certified that error appears in the above-identified patent and that said Letters Patent is hereby corrected as shown below:

Column 24
Line 41, "A multifunctional testing device (DL) composed of a" should read --34. A multifunctional testing device (DE) composed of a--.

Column 24
Line 62, "(I1,12) and outlets (O1, O2)" should read, --(I1, I2) and outlets (O1, O2)--.

Signed and Sealed this

Twenty-sixth Day of October, 2010

David J. Kappos
*Director of the United States Patent and Trademark Office*